United States Patent
Müller et al.

(10) Patent No.: US 7,169,589 B2
(45) Date of Patent: Jan. 30, 2007

(54) SILICATEIN-MEDIATED SYNTHESIS OF AMORPHOUS SILICATES AND SILOXANES AND USE THEREOF

(76) Inventors: Werner E. G. Müller, Semmelweissstrasse 12, Wiesbaden (DE) 65203; Heinz C. Schröder, Hans-Bredow-Strasse 37a, Wiesbaden (DE) 65189; Bernd Lorenz, Olvenstedter Chaussee 3, Magdeburg (DE) 39110; Anatoli Krasko, Heugasse 2, Mainz (DE) 55116

( * ) Notice: Subject to any disclaimer, the term of this patent is extended or adjusted under 35 U.S.C. 154(b) by 513 days.

(21) Appl. No.: 10/343,104

(22) PCT Filed: Jul. 20, 2001

(86) PCT No.: PCT/EP01/08423

§ 371 (c)(1),
(2), (4) Date: Jan. 27, 2003

(87) PCT Pub. No.: WO02/10420

PCT Pub. Date: Feb. 7, 2002

(65) Prior Publication Data

US 2003/0134391 A1 Jul. 17, 2003

(30) Foreign Application Priority Data

Jul. 28, 2000 (DE) .............................. 100 37 270

(51) Int. Cl.
*C12P 3/00* (2006.01)
*C12P 21/06* (2006.01)
*C12N 1/21* (2006.01)
*C12N 1/19* (2006.01)
*C12N 5/06* (2006.01)
*A01N 55/10* (2006.01)
*C07H 21/04* (2006.01)

(52) U.S. Cl. ..................... 435/168; 435/69.1; 435/350; 435/183; 435/189; 435/252.33; 435/252.3; 435/254.11; 435/94.3; 424/724; 536/23.2

(58) Field of Classification Search ................ 435/168, 435/252.3, 252.33; 536/23.2, 350
See application file for complete search history.

(56) References Cited

FOREIGN PATENT DOCUMENTS

WO WO- 00 35993 A 6/2000

OTHER PUBLICATIONS

Cha et al., PNAS 96:361-365, 1999.*
Shimizu K, et al. "Silicatein Alpha: Cathepsin L-Like Protein In Sponge Biosilica" Proc. Natl. Acad. Sci. USA vol. 95, pp. 6234-6238, May 1998 Genetics; XP002924682.
Cha J N, et al. "Silicatein Filaments and Subunits From A Marine Sponge Direct The Polymerization of Silica and Silicones in Vitro" Proc. Natl. Acad. Sci. USA vol. 96, pp. 361-365, Jan. 1999 Biochemistry; XP-001037314.
Ogino,et al. "Function of The Propeptide region in Recombinant Expression of Active Procathepsin L in *Escherichia Coli*" J. Biochem. 126, 78-83 (1999) XP-002190291.
Zhou, et al. "Efficient Catalysis of Polysiloxane Synthesis by silicatein Alpha Requires Specific Hydroxy and Imidazole Functionalities"Angew. Chem. Int. Ed. 1999, 38, No. 6 RP 779-782 (1999) XP-001026439.
Krasko, et al. "Expression of Silicatein and Collagen genes in the Marine Sponge *Suberites domuncula* is Controlled by Silicate and Myotrophin" Eur. J. Biochhem. 267, 4878-4887 (2000); XP-002190292.
F. Liebau, "Structural Chemistry of Silicates", Springer-Verlag 1985, Berlin, ISBN 0-387-13747-5, pp. 1-347.
A. Petzold et al., "Silikatchemie", Ferdinand Enke Verlag, Stuttgart 1979, ISBN 3-432-90061-9 (discussed in specification), pp. 5-219.
Roempp Chemie Lexikon, Georg Thieme Verlag Stuttgart/New York, vol. 5, 9the edition, pp. 3568-3571, 4152-4155 and 4160-4175 (discussed in specification).
A. Skorokhod et al., "Immunochemical Localization of the phylogenetically oldest Receptor Tyrosine Kinase: Existence in the Marine Sponge *Geodia Cydonium*", Cellular and Molecular Biology, 1997, 43 (4), pp. 509-519.
N. Kroeger et al., "Frustulins: domain conservation in a protein family associated with diatom cell walls", 1996, Eur. J. Biochem. 239, pp. 259-264.
L. A. Ostermann, "Methods of Protein and Nucleic Acid Research", Springer-Verlag Berlin 1986, vol. 3, pp. 47-52 and pp. 408-412.
B. D. Ratner et al., "Biomaterials Science, An Introduction to Materials in Medicine", Academic Press, San Diego, 1996, pp. 105-116.
E. P. Pleuddemann, "Chemistry of Silane Coupling Agents", Silylated Surfaces, 1980, Gordon & Breach Science Publishers, New York, pp. 31-53.
Parfuemerie und Kosmatik, vol. 67, Nr. 4, 1986, pp. 232-241; Nr. 5, 1986 pp. 326-334; Nr. 6, 1986 pp. 384-389; Nr. 4, 1987, pp. 195-203, discussed in specification.

(Continued)

Primary Examiner—Rebecca E. Prouty
Assistant Examiner—Iqbal Chowdhury
(74) Attorney, Agent, or Firm—Saliwanchik, Lloyd & Saliwanchik (57) ABSTRACT

Silicatein is an enzyme of silicate-forming organisms used for the synthesis of their silicate scaffold. The present invention relates to the use of highly-expressed and highly active recombinant silicatein, silicatein isolated from natural sources after gene induction as well as silicatein-fusion proteins for the synthesis of amorphous silicon dioxide (silicic acids and silicates), siloxanes as well as modification of these compounds and their technical use.

26 Claims, 5 Drawing Sheets

OTHER PUBLICATIONS

E. P. Pleuddemann, "Silane Compounds for Silylating Surfaces", Silanes, Surfaces and Interfaces, 1986, Gordon and Breach Science Publishers, New York, pp. 1-24.

Wilhelm Hinz: "Silicat-Lexikon", 2nd vol., Akademie-Verlag, Berlin, 1985 (discussed in specification).

Frederick M. Ausubel et al., "Current Protocols in Molecular Biology", vol. 2; Article 1, Section 1.4; Article 2, Section 1.5; and Article 5, Sections 5.0, 5.2, 5.5 and 5.9; John Wiley and Sons, Inc., New York, 2002 (discussed in specification).

Frederick M. Ausubel et al.: "Current Protocols in Molecular Biology", vol. 3; Article 16, Sections 16.0-16.2, and 16.5; John Wiley and Sons, Inc., New York, 2001 (discussed in specification).

"Chemie in unserer Zeit", vol. 14, pp. 197-207, Wiley-VCH Verlag GmbH & Co, 1980 (discussed in specification).

Reinhold Tacke et al.: "Syntheses and Properties of Bioactive Organo-Silicon Compounds", Topics in Current Chemistry, "Bioactive Organo-Silicon Compounds", vol. 84, Berlin, Springer-Verlag, 1979 (discussed in specification).

* cited by examiner

Figure 1

```
GAGGATAGAAAGTCTACAATCTGTAAGGACAATGCTTGTCACAGTGGTAGTACTGGGTCT    60
                              M  L  V  T  V  V  V  L  G  L    10
ACTGGGGTTTGCTTCTGCAGCCCAGCCCAAGTTTGAATTTGTAGAAGAATGGCAGCTGTG   120
 L  G  F  A  S  A  A  Q  P  K  F  E  F  V  E  E  W  Q  L  W    30
GAAGTCCACTCACTCTAAGATGTACGAGTCACAGTTAATGGAACTCGAAAGACATCTGAC   180
 K  S  T  H  S  K  M  Y  E  S  Q  L  M  E  L  E  R  H  L  T    50
GTGGCTCTCCAATAAGAAATATATCGAGCAACACAATGTCAACTCACACATTTTCGGTTT   240
 W  L  S  N  K  K  Y  I  E  Q  H  N  V  N  S  H  I  F  G  F    70
TACTCTGGCAATGAACCAGTTTGGAGATCTGAGTGAATTGGAGTATGCTAACTATCTTGG   300
 T  L  A  M  N  Q  F  G  D  L  S  E  L  E  Y  A  N  Y  L  G    90
CCAGTATCGCATTGAGGATAAAAAATCTGGCAACTACTCAAAGACTTTTCAGCGTGATCC   360
 Q  Y  R  I  E  D  K  K  S  G  N  Y  S  K  T  F  Q  R  D  P   110
TCTACAGGACTACCCTGAAGCTGTAGACTGGAGAACCAAAGGAGCTGTCACGGCTGTCAA   420
 L  Q  D  Y  P  E  A  V  D  W  R  T  K  G  A  V  T  A  V  K   130
GGACCAGGGAGACTGTGGTGCTAGCTATGCTTTCAGTGCTATGGGTGCTTTGGAGGGTGC   480
 D  Q  G  D  C  G  A  S  Y  A  F  S  A  M  G  A  L  E  G  A   150
TAATGCTTTAGCCAAGGGAAATGCAGTATCTCTCAGTGAACAGAACATCATTGATTGCTC   540
 N  A  L  A  K  G  N  A  V  S  L  S  E  Q  N  I  I  D  C  S   170
GATTCCTTACGGTAACCACGGTTGTCATGGAGGCAATATGTATGATGCTTTTTTGTATGT   600
 I  P  Y  G  N  H  G  C  H  G  G  N  M  Y  D  A  F  L  Y  V   190
CATCGCTAACGAGGGGGTCGATCAGGACAGTGCATATCCATTTGTAGGAAAGCAATCCAG   660
 I  A  N  E  G  V  D  Q  D  S  A  Y  P  F  V  G  K  Q  S  S   210
CTGCAACTATAATAGTAAATACAAAGGTACATCAATGTCGGGGATGGTGTCAATCAAAAG   720
 C  N  Y  N  S  K  Y  K  G  T  S  M  S  G  M  V  S  I  K  S   230
TGGTAGTGAGTCTGACTTACAAGCAGCTGTTTCAAACGTTGGCCCTGTATCTGTTGCTAT   780
 G  S  E  S  D  L  Q  A  A  V  S  N  V  G  P  V  S  V  A  I   250
TGATGGTGCTAACAGTGCCTTCAGGTTTTACTACAGTGGTGTCTATGACTCATCACGATG   840
 D  G  A  N  S  A  F  R  F  Y  Y  S  G  V  Y  D  S  S  R  C   270
CTCTAGTAGTAGTCTTAACCACGCAATGGTAGTCACTGGATACGGATCATACAATGGGAA   900
 S  S  S  S  L  N  H  A  M  V  V  T  G  Y  G  S  Y  N  G  K   290
AAAATACTGGCTGGCCAAGAATAGCTGGGGAACTAACTGGGGTAACAGTGGCTATGTGAT   960
 K  Y  W  L  A  K  N  S  W  G  T  N  W  G  N  S  G  Y  V  M   310
GATGGCTCGCAACAAGTACAACCAGTGTGGAATTGCTACCGATGCATCTTATCCCACCCT  1020
 M  A  R  N  K  Y  N  Q  C  G  I  A  T  D  A  S  Y  P  T  L   330
ATAAACTTATATATATATAGTCTTAGAAACATTATCCTTTTCTTTACCCTTGTCTCTATA  1080
GGCCATAGAGTGATTGTAGGCTGTTTGCATTTGATGACTGTATATACCCTATCATTTTTT  1140
GTGATTCTATCTGATTAAAAATCCCATACCCGACCAAACCATCAATTTATCAAATCATGA  1200
```

Figure 2

```
SILCA_SUBD : MLVTVVVLGLLGFASAAQPKFEFVEEWQLWKSTHSRMYESQLMELERHLTWLSNKK :  56
                                                              Propeptide —|—
SILCA_SUBD : YIEQHNVNSHIFGFTLAMNQFGDLSELEYANYLGQYRIEDKKSGNYSKTFQRDPLQ : 112
                                                CT
             —|— Mature Proteine  •  ▼
SILCA_SUBD : DYPEAVDWRTKGAVTAVKDQGDCGASYAFSAMGALEGANALAKGNAVSLSEQNIID : 168

•    •                          •
SILCA_SUBD : CSIPYGNHGCHGGNMYDAFLYVIANEGVDQDSAYPFVGKQSSCNYNSKYKGTSMSG : 224
                                                         CT
                                                      •  ▼
SILCA_SUBD : MVSIKSGSESDLQAAVSNVGPVSVAIDGANSAFRFYYSGVYDSSRCSSSSLNHAMV : 280
                          CT
                          ▼                  •
SILCA_SUBD : VTGYGSYNGKKYWLAKNSWGTNWGNSGYVMMARNKYNQCGIATDASYPTL : 330
```

A. Fusion protein (chimeric-protein)

B. Separate protein-expression I

C. Separate protein-expression II (cassette-expression)

SEQUENCE LISTING

<160> NUMBER OF SEQ ID NOS: 2

<210> SEQ ID NO 1
<211> LENGTH: 1200
<212> TYPE: DNA
<213> ORGANISM: Suberites domuncula

<400> SEQUENCE: 1

```
gaggatagaa agtctacaat ctgtaaggac aatgcttgtc acagtggtag tactgggtct     60
actggggttt gcttctgcag cccagcccaa gtttgaattt gtagaagaat ggcagctgtg    120
gaagtccact cactctaaga tgtacgagtc acagttaatg aactcgaaa gacatctgac     180
gtggctctcc aataagaaat atatcgagca acacaatgtc aactcacaca ttttcggttt    240
tactctggca atgaaccagt ttggagatct gagtgaattg agtatgcta actatcttgg     300
ccagtatcgc attgaggata aaaatctgg caactactca aagactttc agcgtgatcc      360
tctacaggac taccctgaag ctgtagactg gagaaccaaa ggagctgtca cggctgtcaa    420
ggaccaggga gactgtggtg ctagctatgc tttcagtgct atgggtgctt tggagggtgc    480
taatgcttta gccaagggaa atgcagtatc tctcagtgaa cagaacatca ttgattgctc    540
gattccttac ggtaaccacg ttgtcatgg aggcaatatg tatgatgctt ttttgtatgt     600
catcgctaac gaggggtcg atcaggacag tgcatatcca tttgtaggaa agcaatccag     660
ctgcaactat aatagtaaat acaaaggtac atcaatgtcg gggatggtgt caatcaaaag    720
tggtagtgag tctgacttac aagcagctgt ttcaaacgtt ggccctgtat ctgttgctat    780
tgatggtgct aacagtgcct tcaggttta ctacagtggt gtctatgact catcacgatg     840
ctctagtagt agtcttaacc acgcaatggt agtcactgga tacggatcat acaatgggaa    900
aaaatactgg ctggccaaga atagctgggg aactaactgg ggtaacagtg gctatgtgat    960
gatggctcgc aacaagtaca accagtgtgg aattgctacc gatgcatctt atcccaccct   1020
ataaacttat atatatatag tcttagaaac attatccttt tctttaccct tgtctctata   1080
ggccatagag tgattgtagg ctgtttgcat ttgatgactg tatatacct atcattttt    1140
gtgattctat ctgattaaaa atcccatacc cgaccaaacc atcaatttat caaatcatga  1200
```

<210> SEQ ID NO 2
<211> LENGTH: 330
<212> TYPE: PRT
<213> ORGANISM: Suberites domuncula

<400> SEQUENCE: 2

Met Leu Val Thr Val Val Leu Gly Leu Leu Gly Phe Ala Ser Ala
1               5                   10                  15

Ala Gln Pro Lys Phe Glu Phe Val Glu Glu Trp Gln Leu Trp Lys Ser
            20                  25                  30

Thr His Ser Lys Met Tyr Glu Ser Gln Leu Met Glu Leu Glu Arg His
        35                  40                  45

Leu Thr Trp Leu Ser Asn Lys Lys Tyr Ile Glu Gln His Asn Val Asn
    50                  55                  60

Ser His Ile Phe Gly Phe Thr Leu Ala Met Asn Gln Phe Gly Asp Leu
65                  70                  75                  80

Ser Glu Leu Glu Tyr Ala Asn Tyr Leu Gly Gln Tyr Arg Ile Glu Asp
                85                  90                  95

Lys Lys Ser Gly Asn Tyr Ser Lys Thr Phe Gln Arg Asp Pro Leu Gln

-continued

```
                    100                 105                 110
Asp Tyr Pro Glu Ala Val Asp Trp Arg Thr Lys Gly Ala Val Thr Ala
        115                 120                 125
Val Lys Asp Gln Gly Asp Cys Gly Ala Ser Tyr Ala Phe Ser Ala Met
130             135                 140
Gly Ala Leu Glu Gly Ala Asn Ala Leu Ala Lys Gly Asn Ala Val Ser
145             150                 155                 160
Leu Ser Glu Gln Asn Ile Ile Asp Cys Ser Ile Pro Tyr Gly Asn His
                165                 170                 175
Gly Cys His Gly Gly Asn Met Tyr Asp Ala Phe Leu Tyr Val Ile Ala
            180                 185                 190
Asn Glu Gly Val Asp Gln Asp Ser Ala Tyr Pro Phe Val Gly Lys Gln
        195                 200                 205
Ser Ser Cys Asn Tyr Asn Ser Lys Tyr Lys Gly Thr Ser Met Ser Gly
    210                 215                 220
Met Val Ser Ile Lys Ser Gly Ser Glu Ser Asp Leu Gln Ala Ala Val
225             230                 235                 240
Ser Asn Val Gly Pro Val Ser Val Ala Ile Asp Gly Ala Asn Ser Ala
            245                 250                 255
Phe Arg Phe Tyr Tyr Ser Gly Val Tyr Asp Ser Ser Arg Cys Ser Ser
            260                 265                 270
Ser Ser Leu Asn His Ala Met Val Val Thr Gly Tyr Gly Ser Tyr Asn
        275                 280                 285
Gly Lys Lys Tyr Trp Leu Ala Lys Asn Ser Trp Gly Thr Asn Trp Gly
        290                 295                 300
Asn Ser Gly Tyr Val Met Met Ala Arg Asn Lys Tyr Asn Gln Cys Gly
305             310                 315                 320
Ile Ala Thr Asp Ala Ser Tyr Pro Thr Leu
                325                 330
```

SILICATEIN-MEDIATED SYNTHESIS OF AMORPHOUS SILICATES AND SILOXANES AND USE THEREOF

BACKGROUND OF THE INVENTION

Silicon is the second-most element of the earth's crust (more than 80% of the earth's crust consist out of silicates) and is present in all forms of different compounds. Silicon compounds do not only represent most of the species of this class of minerals, but are also very important from an economical point of view. They are used in large scales and diverse forms. Glass, porcelain, emaillie, clay products, cement and water glass are technically important materials that consist out of silicates. The catalytic properties of some of the silicates are used synthetically. Their versatile uses are further expanded, if other elements, in particular aluminium, occupy some of the lattice positions that are otherwise occupied by silicon. Feldspars and zeolithes, for example, belong to these alumo silicates; the importance of the latter is based in particular in their molecular sieve and ions exchange properties. Al- and Ca-silicates have become important as filling materials in the laque-, rubber-, plastics- and paper-industry, Mg-silicate (talcum) as an absorber and filling material in cosmetics and pharmaceuticals and alkali-aluminium-silicates as exchange for phosphates in cleaning agents. For the setting of Portland cement, silicates play an important role. Since some silicates carry free OH-groups (analogous to the silanoles) on their surfaces, one can bind reactive groups thereto; these properties are used for immobilisation in the solid phase-technique.

1. 1. Silicon Dioxide

Silicon dioxide ($SiO_2$) is a solid with a high melting point, which is present both in crystallised and amorphous forms. In all these forms of appearances, each silicon atom is tetraedrically surrounded by four oxygen-atoms (coordination number: 4). When crystallised, silicondioxide is present in different modifications (quartz, tridymite, cristobalite and others). The most common form of crystalline $SiO_2$ is quartz. Amorphous silicon dioxide minerals are, amongst others, achat, opal and flintstone. Quartz glass that is obtained by melting of quartz and slow cooling of the melted material does not anymore exhibit crystal surfaces. It is used for, amongst others, the production of quartz lamps (because of its permeability for ultraviolet radiation), and heat resistant apparatuses. Furthermore, the shells of diatoms (diatomeen) consist out of amorphous $SiO_2$.

1.2. Silicic Acids and Silicates

Silicon exhibits the coordination number 4 also in silicic acid and silicates. The tetraedrically-built $[SiO_2]^{4-}$-ion tends to polymerisation by of $SiO_4$-subunits. In this case, two Si-atoms are bound to another linking by one O-atom.

From ortho-silicic acid, at first ortho-disilicic acid (pyro-silicic acid; $H_6Si_2O_7$) is formed by splitting off water (condensation). Further condensation leads to the meta-silicic acids $[(H_2SiO_3)]_n$ via the poly-silicic acids. In case of smaller numbers of $SiO_4$-units (n=3, 4 or 6), by this also ring-shaped molecules can be formed.

The poly-silicic acids have an amorphous (unordered) structure.

The salts of the ortho-disilicic acids (ortho-silicates), having the structure $Me_2SiO_4$, contain single $[SiO_4]^{4-}$ anions. The water-soluble alcalisilicates which can be obtained, for example, by melting of quarz with soda, brine or potassium carbonate, in addition to $[SiO_4]^{4-}$ anions, contain also $[Si_2O_7]^{6-}$ and $[Si_3O_{10}]^{8-}$ anions (and larger anions). Such "water glass" solutions, from which the solubilized particles can be separated by dialysis at a membrane are suited, amongst others, for the cementation of glass and porcelain, for the impregnation of paper, as flame protective agent for wood and for the conservation of foods.

After the acidification of such an alkalisilicate solution, the acid molecules that have been formed out of the $[SiO_4]^{4-}$ and $[Si_2O_7]^{6-}$ groups (and larger groups) by proton uptake, condensate with each other to form poly-silicic acids (see above), whereby the solution becomes gel-like. The polymers obtained at first consist out of chains or networks. Upon further progress of the condensation, three-dimensional structures are formed, which correspond to the composition $SiO_2$.

The following classification can be obtained:
1. Silicates with discrete anions:
   a) Island-silicates: These are ortho-silicates with the anion $[SiO_4]^{2-}$. Example: phenacit, olivin, zirconium.
   b) Group-silicates: The $SiO_4$-tetraeders are linked to form short chain units. Examples: di-silicates with the anion $[Si_2O_7]^{6-}$ and tri-silicates.
   c) Ring-silicates: The $SiO_4$-tetraeders are arranged in ring form. Examples: benitoid (3-ring), axinite (4-ring), beryll (6-ring).
2. Chain-silicates and ribbon-silicates. Chain-silicates consist out of chain-like $SiO_4$-tetraeders bound to each other; they are polymers of the anions $[SiO_3]^{2-}$. By linking several $SiO_4$-chains, ribbon-like molecules can be formed. Examples: hornblende, asbestos.
3. Layer-silicate (sheet-silicate): Layer-silicates contain even sheets made of $SiO_4$ tetraeders. These are held together by cations stored in-between. They are polymers of the anions $[Si_4O_{10}]^{4-}$. Examples: talcum, caolinit.
4. Scaffold-silicates: In the scaffold-silicates, the tetraedic $SiO_4$-groups are bound to three-dimensional lattices. Examples: different modifications of silicon dioxide, like feldspatuses.

The condensation process that leads to the polysilicic acids or polysilicates, respectively, can be controlled by partial replacement of the OH-groups of the silicic acid by single-binding organyl residues, which do not participate in the condensation process (production of different silicones).

Synthetic silicic acids are amorphous, non-poisonous, and, in contrast to the crystalline $SiO_2$ modification, do not lead to the generation of a silicose.

General literature:

Hinz, Silicat-Lexikon ($2^{nd}$ vol.), Berlin: Adademie Verl. 1985

Liebau, Structural Chemistry of Silicates, Berlin: Springer 1985

Petzold and Hinz, Einführung in die Grundlagen der Silicatchemie, Stuttgart: Enke 1979

CD Römpp Chemie Lexikon—Version 1.0, Stuttgart/N.Y.: Georg Thieme Ver lag 1995

1.3. Siloxanes, Silicones

The methods that are used for the demonstration of silanoles and siloxanes according to the state of the art consist in that water is acting on organic silicon derivatives, such as trimethyl silicium chloride $[(CH_3)_3SiCl]$, whereby first silanoles, such as trimethyl silanole, are formed:

From these, siloxanes, such as hexamethyl disiloxane $[(CH_3)_3Si—O—Si(CH_3)_3]$ are generated by splitting off water:

Furthermore, compounds of high molecular weight with ring- or chain-like structures or three-dimensionally cross-linked macromolecules ("silicones") can be produced by reacting dimethyl or monomethyl silicon chloride with water (via the intermediate products dimethyl silanediol or methyl silanetriol, respectively):

The starting compounds $R_3SiOH$ (silanoles), $R_2Si(OH)_2$ (silandioles) and $RSi(OH)_3$ (silantrioles) as used for the demonstration of additional silicones, are commonly produced by hydrolysis of the respective halogene compounds $R_3SiCl_2$, and $R_2SiCl_3$ (R=ethyl, propyl, phenylgroups and others).

Accordingly, siloxanes (silicones) can be grouped into:
a) linear polysiloxanes of the type $R_3SiO[R_2SiO]_nSiR_3$.
b) branched polysiloxanes which contain tri-functional or tetra-functional siloxane-units at their branching sites.
c) cyclic polysiloxanes which are built of bi-functional siloxane-units.
e) crosslinked polymers, wherein chain- or ring-form molecules are linked into two- or three-dimensional networks.

The viscosity of the high molecular weight silicones (silicone oils), which consist of chain-form macromolecules, increases with increasing chain length. Silicones play an important role as technical materials. Chains that are crosslinked to a low extent exhibit rubber-elasticity (silicone rubber; use: sealings and others), silicones that are highly cross-linked are resin-like (silicone resins).

Due to their hydrophobic (water-repellent) properties based on their organic portion, silicones are used for impregnation purposes (of textiles, paper and others).

SUMMARY OF THE INVENTION 1.4. Silicatein

Some of the above-mentioned silicon compounds can only be produced in a cost-intensive manner or are present only in small amounts as mineral resources, respectively, and can therefore only be isolated with considerable effort. The process of the chemical synthesis of silicates requires drastic conditions, such as high pressure and high temperature.

In contrast, with the aid of specific enzymes, organisms (in particular sponges and algae) are able to form silicate scaffolds under natural conditions, i.e. at low temperature and low pressure. The advantages of this pathway are: high specificity, coordinated formation, adjustability, and the possibility for synthesizing nanostructures.

The isolation and purification of a silicate-forming enzyme (silicatein) was recently described for the first time: Shimizu, K., et al., Proc. Natl. Acad. Sci. USA 95: 6234–6238 (1998).

Nevertheless, this results in the problem that the isolation and the purification of the enzyme (silicatein) is time-consuming and laborious, and that only relatively low amounts can be achieved.

One possible approach is the synthesis of the recombinant protein (recombinante silicatein) with the aid of the known cDNA- or gene-sequence. This allows for the effective enzymatic synthesis of silicates.

In case of the production of the recombinant silicateins from the sponges *Suberites domuncula* and *Tethya aurantia*, the problem occurred that by using the methods according to the state of the art only very low yields could be achieved and that the recombinant protein exhibited only low enzymatic activity. The present invention describes that, by specific modification of the expression conditions, recombinant silicatein can be produced in high yields and with high specific activity. Furthermore, the modified recombinant enzyme exhibits a higher pH and temperature stability than the natural one and the recombinant one having a complete cDNA-sequence. The modified recombinant protein furthermore exhibits an enzymatic activity over a broad pH (4.5–10), in contrast to the natural and recombinant protein with complete cDNA-sequence that is active at pH-values in the neutral range (pH 7.0).

By way of production of a specific polyclonal antibody and subsequent coupling to a solid phase, a fast and effective affinity-chromatography purification of the enzyme can be achieved.

The use of fusion proteins and the application of different starting substrates lead to numerous possibilities for variations and technical applications.

BRIEF DESCRIPTION OF THE DRAWINGS

FIG. 1 shows a cDNA together with deduced amino acid sequence for the suberites domuncula-silicatein.

2. Production of Silicatein 2.1. Production of Recombinant Silicatein 2.1.1. Cloning of the cDNA from Marine Sponges

DETAILED DESCRIPTION

The silicatein protein derived from sponges contains characteristic sequence portions, several of which shall be mentioned: region around the serine-rich amino acid-cluster (in case of *S. domuncula*: amino acids 267–277); region around the cysteine, the first amino acid of the catalytic triade (in case of *S. domuncula*: amino acid 138), which is absent in silicatein and present in the related enzymes cathepsines; region around the transition between propeptide and the processed peptide (in case of *S. domuncula*: amino acids 112/113).

The gene for silicatein can be identified from cDNA-libraries by using the technique of the polymerase-chain reaction, e.g. in ZapExpress and in *Escherichia coli* XL1-Blue MRF', using suitable degenerated primers (for example: reverse primer 5'-GAA/GCAG/CCGIGAIGAA/GTCA/GTAG/CAC-3' together with the 5'-vector-specific primer [region around amino acids 267–277]—or the forward primer at the same protein-segment together with the 3'-vector-specific primer); for this, a corresponding vector-specific primer is used. The sythesis product obtained in this way is used for screening in the respective cDNA-library. Thereafter, the identified clone(s) is/are sub-cloned into a vector (for example pGem-T) and subsequently sequenced. As an example, FIG. 1 depicts the cDNA for silicatein of *Suberites domuncula*.

2.1.2. Expression and Isolation of the Recombinant Silicatein

The production of recombinant silicatein is preferably performed in *E. coli* XL1-Blue. Nevertheless, the production in yeast and in mammalian cells is possible and was successfully performed. For this, the cDNA is cloned into a corresponding vector, e.g. pQE-30. In addition, other expression vectors have proven to be suitable as well. After transformation of *E. coli*, the expression of silicatein is usually performed by induction with IPTG (isopropyl-β-D-thiogalactopyranoside) (Ausubel, F. M., Brent, R., Kingston, R. E., Moore, D. D., Smith, J. A., Seidmann, J. G. and Struhl, K., (1995) *Current Protocols in Molecular Biology*, John Wiley and Sons, New York). The expression of silicatein as well as the purification of the recombinant proteins using, e.g., the histidin-tag present at the recombinant protein, can be performed on the corresponding affinity columns, e.g. a Ni-NTA-matrix (Skorokhod, A., Schäcke, H., Diehl-Seifert, B., Steffen, R., Hofmeister A., and Müller W. E. G. *Cell. Mol. Biol.* 43:509–519; 1997).

Figure 2:
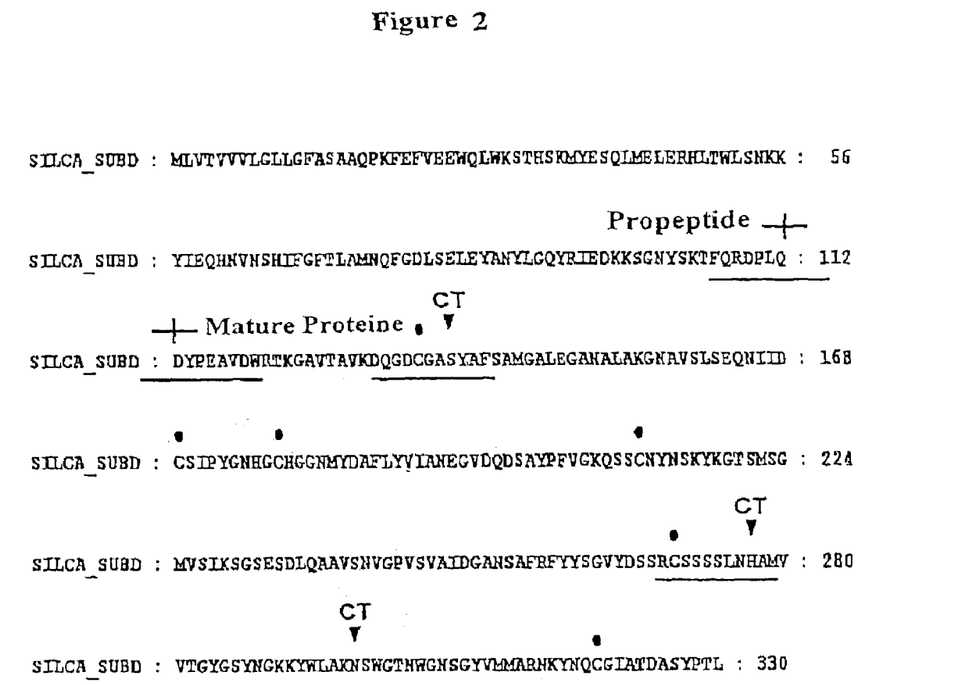
FIG. 2 shows an amino acid sequence of silicatein from the sponge suberites domuncula.

The expression of the complete sequence of silicatein in *E. coli* can, nevertheless, only be achieved with very low yields. The following modifications of the expression conditions surprisingly led to drastic improvements of said yield:

1. By truncating the sequence coding for the N-terminal end of the protein, a more than 100-fold increase of the expression (in comparison to the expression of the complete cDNA) was achieved. Preferrably, the start is put into the region of the propeptide. Nevertheless, also a truncation in the region of the "ripe" protein in front of the first potential disulfide bridge (commonly at the amino acid 135) leads to the desired strong expression (FIG. 2).
2. Furthermore, a more than 20-fold increased expression of silicatein could be achieved using a truncated cDNA that codes for the C-terminal end of the protein, in comparison to the expression of the complete cDNA (FIG. 2). The truncation of the gene at its 3'-end in the region of the sequence behind the last potential disulfide bridge (commonly at the amino acid 319) has proven to be successful as well. There, a stop-codon is inserted.
3. A more than 40-fold increase of the expression in *E. coli* is achieved by adding a protease inhibitor-cocktail during the lysis of the cells. The following protease inhibitor-cocktails have been advantageously used: antipain (10 µg), bestatin (5 µg/ml), chymostatin (10 µg/ml), leupeptin (1 µg/ml), pepstatin (1 µg/ml), aprotinin (1 µg/ml). This step was particularly unexpected, since the protocol that is commonly used for the isolation of the recombinant proteins, like in the Bug-Buster extration kit (Novagen), does not provide for this.
4. After the lysis of the *E. coli*-bacteria, the resulting solution is very viscous. An efficient isolation of the recombinant protein is achieved by the addition of enzymes for the digestion of the nucleic acids. For this, the nuclease "benzonase" is suited.
5. In case of an expression of silicatein in *E. coli*, commonly, the recombinant protein is found in the "inclusion bodies". Therefore, the recombinant protein must be converted in its "native" form. For this, the following method has proven to be suitable: the *E. coli*-bacteria are lysed using a solution of the Bug-Buster extraction kit; after washing, the "inclusion bodies" are recovered by centrifugation. The "inclusion bodies" are washed several times using the so-called IB Wash Buffer of the "Protein Refolding Kit (Novagen)". The instructions as supplied with the, e.g., "Protein Refolding Kit" are used in order to convert the recombinant silicatein in its "native" form. Using this and other comparable methods, the recombinant silicatein will, nevertheless, be degraded. Surprisingly, this process can be avoided by the omission of the enzyme lysozym. Commonly, this lysozym step is a fixed step in a protocol for the extraction of recombinant proteins from *E. coli*. Its function is, to remove associated bacterial membranes from the recombnant proteins. The final purification of the recombinant silicatein can be performed using affinity matrices, such as Ni-NTA matrices.

Figure 3:
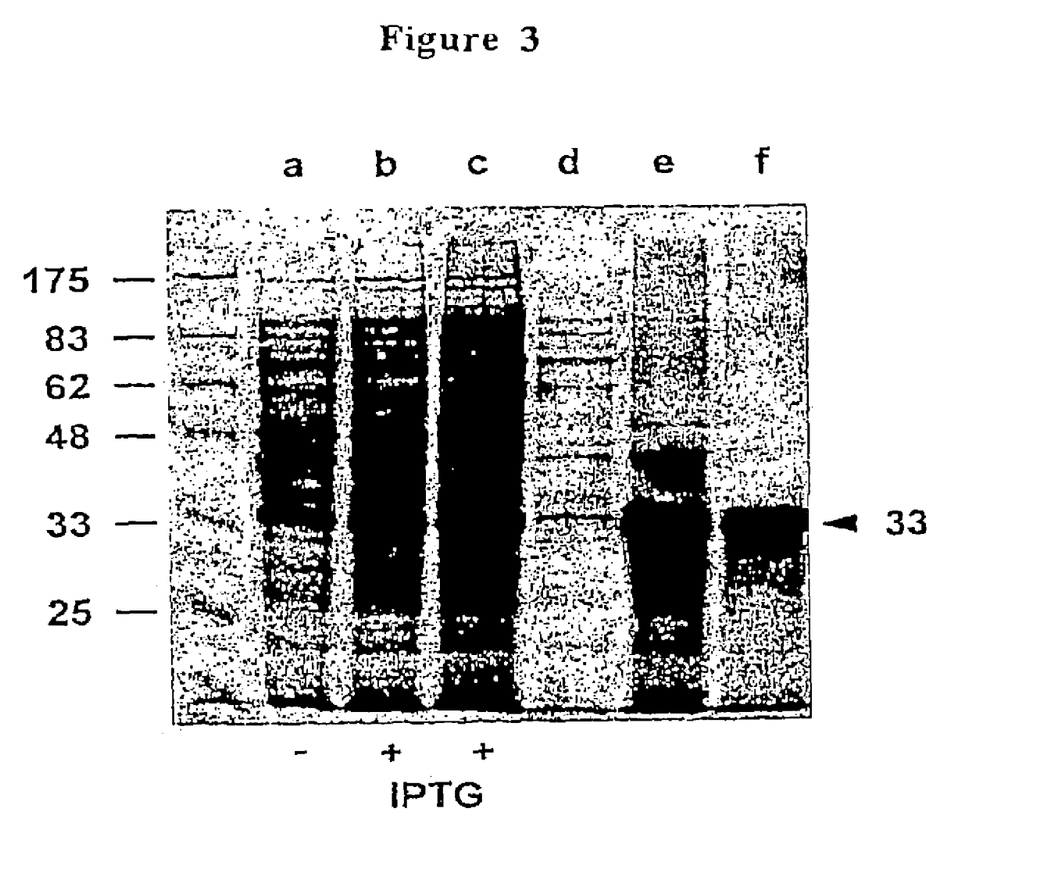
FIG. 3 illustrates the production of a recombinant silicatein-protein in *E. coli*.

After application of these amendments of the method, a surprisingly high expression in *E. coli* is achieved (more than 100-fold); now, yields of approximately 10 mg/100 ml bacterial culture medium of recombinant silicatein can be achieved (FIG. 3).

2.1.3. Expression and Isolation of the Recombinant Silicatein from Other Silicate-Forming Organisms.

According to the procedure as described above, the isolation, cloning and expression of the cDNA for silicatein from additional silicon dioxide-producing organisms can be performed, for example from diatoms (e.g. *Cylindrotheca fusiformis*). The extraction of diatoms in axenic cultures is state of the art (Kröger, N. Bergsdorf, C. and Sumper M. *Europ. J. Biochem.* 239:259–264; 1996).

2.2 Isolation and Purification of Silicatein from Animals and Single Cell-Organisms Silicatein is the enzyme that synthesizes amorphous silicate, e.g. in sponges. Therefore, silicatein can be obtained from said organisms. For this, e.g. the spiculae (consisting of amorphous silicate) from the sponge *Suberites domuncula* can be obtained by dissociation of the tissue in $Ca^{++}$ and $Mg^{++}$-free seawater. The spiculae are obtained by sedimentation. The amorphous silicate of the spiculae is removed in alcalic milieu, e.g. in diluted sodium hydroxide. The organic fibrilles of the spiculae, which contain the silicatein, are obtained by centrifugation (e.g. 20,000×g; 1 hour; 4° C.). The protein is brought in solution by high salt concentration, such as e.g. 1 M NaCl, but also by means of the "Protein Refolding-Kit".

Subsequently, the silicatein is purified on an affinity matrix. The affinity matrix is produced by immobilizing a silicatein-specific antibody onto a solid phase (CNBr-activated sepharose or other suitable carriers), and purified. As antibodies monoclonal or polyclonal antibodies against the silicatein are used which are produced according to standard methods (Osterman, L. A. Methods of Protein and Nucleic Acid Research Vol. 2; Springer-Verlag [Berlin] 1984). The coupling of the antibody to the matrix of the column is performed according to the recommendations of the manufacturer (Pharmacia). The elution of the pure silicatein takes place by means of a pH-shift or shift of the ionic strength. In addition, other affinity matrices, such as polymer silicates oder polymer silicates/germanates, have been successfully used. The elution of the silicatein from these matrices takes place at a pH at the isoelectric point of silicatein (in case of the *S. domuncula*-silicatein at a pH of approximately 6).

Analogous isolations of silicatein from other silicon dioxide-producing organisms, such as diatoms (e.g. *Cylindrotheca fusiformis*) have been performed according to the above-depicted method.

Furthermore, the invention is novel in that the silicatein-gene can be induced with suitable silicate concentrations in medium (commonly 60 µM) and by myotrophin (1 µg/ml) (FIGS. 4A,B).

3. Detection of Silicatein-Activity and Synthesis of Silicon-Alkoxy-Compounds

Measuring the enzymatic activity of the recombinant silicatein is usually performed as follows. The recombinant silicatein is dialysed over night against a buffer that is suitable for the reaction, such as 25 mM Tris-HCl, pH 6.8 (other buffers within the pH-ranges of 4.5 to 10.5 are also suited).

Commonly, 1–60 µg of recombinant silicatein are solubilized in 1 ml of a suitable buffer, such as 25 mM Tris-HCl (pH 6.8) and 1 ml of usually, 1–4.5 mM tetraethoxysilane-solution. The enzymatic reaction can be performed at room temperature—but also at temperatures between 5° C. and about 65° C. The average time of incubation is 60 min. During this time-span, usually 300 nmoles of amorphous silicate per 100 µg silicatein are synthesised (as molybdate-reactive soluble silicate). For the detection of the silicate products, the material is centrifuged in a desk centrifuge (12 000×g; 15 min; +4° C.), washed with ethanol and air-dried. Subsequently, the sediment is hydrolysed with e.g. 1 M NaOH. Silicate that is developed is quantitatively measured in the solution using a molybdate-supported detection method, such as e.g. the silicone-assays (Merck).

Surprisingly, it could be found that in addition to the substrate tetraethoxysilane, silicatein further polymerises additional silane-alkoxides.

The method according to the invention is novel in that the following compounds can be used for the silicatein-mediated syntheses: tetraalkoxysilanes, trialkoxysilanoles, dialkoxysilandioles, monoalkoxysilantrioles, alkyl- or aryl-trialkoxysilanes, alkyl- or aryl-dialkoxysilanoles or alkyl- or aryl-monoalkoxysilandioles or the respective (alkyl-or aryl-substituted) alkoxy compounds of gallium (IV), tin (IV) or lead (IV). Mixtures of these substrates are also recognized by the enzyme, and polymerised. Therefore, also mixed polymers can be produced.

For an increase of the activity of the enzyme silicatein, the substrates, such as tetraethoxysilane, are solubilized in dimethylsulfoxides in a stock solution of commonly 500 mM and subsequently diluted into the desired final concentration.

4. Coupling of cDNA for Silicatein with One or Several cDNA(s) (Open Reading Frames) of Other Proteins 4. 1. Production of Silicatein-Fusion Proteins Fusion proteins with silicatein are obtained as follows. A suitable expression vector (for example pQE-30) is used. The silicatein-cDNA—with e.g. a BamHI-restriction side at the 5'-terminus and e.g. a SalI-restriction side at the 3'-terminus—is produced. The stop codon in the silicatein-cDNA is removed. For this, the PCR-technique is used and primers which exhibit the respective restriction sides, are used for the amplification. The cDNA for the second protein is accordingly obtained, exhibiting at the 5'-terminus the same restriction side as present at the 3'-terminus of the silicatein-cDNA (in the example SalI) and at the 3'-terminus one that is different from the others (e.g. a HindIII-side). In case that internal restriction sides are present in the respective cDNAs, alternative restriction enzymes can be used. In addition, linkers in-between both cDNAs can be employed (FIG. 5A).

These two cDNAs are ligiated, purified and ligiated into the pQE-30 vector (Quiagen) according to standard procedures. The ligation occurs directly after the histidine-tag (approximately 6 histidine-codons). The expression and purification of the fusion protein can be achieved as described above (section 2.1.2).

4.2. Separate Expression I

Alternatively to the method that is described at 4.1., a protease cleavage site (such as e.g. an enterokinase side) can be cloned between the cDNA for the silicatein and the cDNA for the bioactive protein. In this case, a codon for a new start methionine can be inserted in front of the coding region of the gene for the bioactive protein. After expression and purification, the (fusion)-protein is cleaved proteolytically. Now, both proteins are separately present (FIG. 5B).

4.3. Separated Expression II (Cassette-Expression)

Alternatively, both proteins can be expressed on one construct—but separately. For this, in an expression vector the gene for silicate is following the his-tag. A stop codon is inserted at the end of the silicatein cDNA. Between the cDNA of the silicatein and the cDNA for a bioactive protein, a ribosome binding side with a codon for a start methionine is cloned. Again, a his-tag is preceding the cDNA for the bioactive protein. This gene is additionally provided with a stop codon (FIG. 5C).

The his-tags can be deleted when the proteins are used for functional analyses in the respective host cells.

4.4. Extensions

Bacterial as well as eukaryotic cells can be used for the expression as described at 4.1 to 4.3.

The expression as described at 4.1 to 4.3 can also be employed for three or more open reading frames.

5. Uses of the Produced Silicateins and Silicatein Fusion-Proteins 5.1. Use of Silicatein for the Modification of Surfaces of Biomaterials The biological reaction of organisms (or biological extracts/products) to biomaterials (exposed and/or implanted) is ruled to a large extend by their surface structure and chemistry. Therefore, a need for methods for the modification of surfaces of such biomaterials exists. It is always the aim, to preserve the advantagous chemical-physical properties of the biomolecules. Thus, only the outermost surfaces should be modified, since their biological interactions will be affected.

Surface-modified biomaterials (such as, for example, by silicone and siloxan-containing block-copolymers, "silanisation") find their use in influencing the cell adhesion and growth, for the modification of the compatibility of blood or for control of the protein adsorption (reduction of the absorption of contact lenses, pretreatment of ELISA-plates). In particular, the silanisation for a modification of material surfaces can be used for the modification of hydroxylated or amine-rich surfaces, such as, for example, surfaces of glass, silicon, germanium, aluminium, quartz and other metal oxides, which are rich in hydroxyl groups. A literature-overview can be found in: B. D. Ratner et al. (editor) Biomaterials Science—An Introduction to Materials in Medicine. Academic Press, San Diego, 1996.

In doing so, nevertheless, the problem occurs that under the conditions that are applied during the production of these modifications, often harmful (destructive) effects occur for the biomaterials used.

The modifications of biomaterials that are solely based on biochemical reactions using the method of the invention (use of recombinant/purified silicatein) (silicatein-mediated enzymatic synthesis of amorphous $SiO_2$-, siloxan- or siloxan-block-copolymers-containing surfaces) represent a "mild" method in comparison to the physical/chemical methods that are used.

The modified area on the surface of the material should, in most cases, be as thin as possible since modified surface layers, that are too thick, can import the mechanical and functional properties of the materials. This can be achieved in a simple manner by varying the reaction time and the concentration of the substrate in the silicatein-mediated enzymatic reaction.

By means of the silicatein-mediated enzymatic reaction, a plurality of different biomaterials and in fact biomaterials, including polymers, metals, ceramics and glasses can be used that either naturally have a protein (silicatein)-binding surface or which have been made able to bind proteins by a preceding modification.

Silanes can form two kinds of surface-structures. Very thin (monolayer) layers, in case only traces of surface-absorbed water are present or, if more water is present, thicker silane-layers that consist out of Si—O groups which are bound to the surface and of silane-units that form a three-dimensional polymeric network. Such modifications, for example, can be produced by the treatment of hydroxylated surfaces using n-propyl-trimethyoxysilane.

General literature: Pleuddemann, E. P. (1980) Chemistry of silane coupling agents. In Silyated Surfaces (D. E. Leyden, editor) Gordon & Breach, New York, pp. 31–53).

By means of the silicatein-mediated enzymatic reaction, in addition several kinds of surface-structures can be formed on a plurality of different biomaterials—using mild conditions that prevents the biomaterials from damage—wherein, since enzymatically mediated, their synthesis takes place in a control manner.

In particular, the outcome of this is the use of the recombinant or a silicatein being purified from different sources for the production of surface-modifications of biomaterials with silicone-like properties (such as silicone-breast-implants) and in medical implants and endoprothesises, as well as in contact lenses.

5.2. Use of Silicatein for the Encapsulation of Biomolecules

By means of the controlled synthesis of $SiO_2$ or siloxane-coatings using the recombinant or a silicatein being purified from different sources, the outcome of this is a use for the encapsulation of biomolecules (including proteins and nucleic acids) as well as bioactive molecules (including hormones, pharmaca and cytokines), with the aim, to modify or improve their biological properties (such as protease and nuclease resistance, temperature stability) or their release (controlled "drug-delivery", in addition an enablement for a topical drug-delivery).

a) Increasing the protease resistance (and temperature stability) of proteins.

Approach: Covering the protein with a silicatein-coating (for example by cross-linking) that synthesises an $SiO_2$-coating.

b) Increasing the nuclease resistance (and temperature stability) of nucleic acids.

Approach: Covering the nucleic acid with a silicatein-coating (for example by cross-linking) which synthesises an $SiO_2$-coating.

Using the above-described manner, a production of depot-forms for pharmaceuticals (including peptides/proteohormones and cytokines) is possible. For this, the pharmaceuticals (including peptides/proteohormones and cytokines) are first modified by a) cross-linking with silicatein or (in case of proteins)
b) the production of fusion proteins with silicatein.

Then, the silicatein-mediated syntheses of the capsule material will take place.

WO 96/14832 A1 May 23, 1996 (U.S. Pat. No. 9,514,261 Nov. 6, 1995) discloses a method for the production of synthetic liposomes from polyphosphates, in order to for increase the uptake of pharmaceuticals ("drug-delivery"). By design of such a liposome-stabilising coating, using silicatein, the efficiency of the method can be increased.

Furthermore, this results in a use of the recombinant or a silicatein being purified from different sources in the production of new biomaterials (or composite-materials), such as replacement materials for bones or dental replacement materials by co-synthesising polysilicates, silicons or mixed polymers (produced by means of the recombined/purified silicatein) and polyphosphates (produced by means of the recombinant polyphosphate-kinase).

5.3. Use of Silicatein for the Encapsulation of Cells/Tissues in Transplantations The controlled synthesis of $SiO_2$ or siloxane-coatings by means of the recombinant or a silicat being purified from different sources can also be used for the encapsulation of cells in transplantations (improvement of the biocompatibility).

This can be performed by coating the cells with silicatein or via the expression of silicatein-fusion proteins on the cell-surface.

5.4. Use of Silicatein for Surface-Modification (Treatment of Contact Zones) of (Silicon)-Semiconductors or Silicon-Chips and Their Use The recombinant as well as a silicatein being purified from different sources can also be used for the surface-modification of (silicon or germanium)-semiconductors or (silicon or germanium)-biosensor-chips. By this, a connection with cells or other structures consisting of organic material can be achieved. These "matrices" can be used for measuring the electric properties of cells. Such silicatein-modified semiconductors (or silicon-microchips) can also be used as biosensors.

5.5 Use of Silicatein for Synthesis of Silicon-Containing Gems and Semi-Precious Stones The recombinant as well as a silicatein being purified from different sources, is able to form amorphous $SiO_2$. Achat, jaspis, onyx and others belong to the amorphous or fine crystalline modifications of the $SiO_2$ (opals), respectively. The possibility to synthesise amorphous $SiO_2$ with the aim of the recombinant or a silicatein being purified from different sources under controlled conditions, whereby controllably foreign molecules/atoms can be introduced, consequently results in the use of the method according to the invention for the production of the above-mentioned and other gems/semi-precious stones.

With the aid of the recombinant or a silicatein being purified from different sources, it is also possible to apply thin SiO and $SiO_2$-layers onto semiconductor-supports (for the production of integrated circuits) under controlled conditions.

5.6. Use of Silicatein for the Synthesis of Silicon (Gallium-, Tin- or Lead-)-Compounds (Including So-Called Sila-Pharmaca)

Silicon is known as a trace element that is apparently needed for the formation of connective tissues and bones (mineralisation). The production of silicon-organic compounds as a basis for so-called sila-pharmaca (pharmaca, wherein C is replaced with Si, exhibiting differences in the mode of action for the organism) is of medical interest [see: Chem. unserer Zeit 14, 197–207 (1980), as well as: Bioactive Organo-Silicon Compounds (Topics Curr. Chem. 84), Berlin, Springer 1979)]; the synthesis of such compounds using mild (enzymatic) conditions is possible by means of the method according to the invention (use of the recombinant or purified silicatein from different sources).

Additional uses of silicon-compounds being synthesised with the aid of the method according to the invention under mild (enzymatic) conditions (use of the recombinant or purified selicatein from different sources) in medicine and cosmetics are: use of silicon-compounds that are accordingly synthesised as ingredient or basis of ointments, as well as parts of tooth pastes [for use in cosmetics, see: Parfüm. Kosmet. 67, 232–239, 326–336, 384–389 (1986); 68,195–203 (1987)].

The silicon-compounds that are synthesised with the aid of the methods according to the invention under mild (enzymatic) conditions (use of the recombinant or silicateines being purified from different sources) can be also used for additional purposes: lubricants (processing of plastics), grease (plastic gears), anti-foaming compounds, mold release agents (providing hydrophobicity to glass, ceramics, textiles, leather) and dielectrica (e.g. in transformators).

The compounds as synthesised with the aid of the method according of the invention also include the siloxane-resins that are used in standard techniques, such as (more or less cross-linked) polymethyl or polymethylphenylsiloxanes.

The silantrioles $RSi(OH)_3$ formed by condensation during the course of the silicatein-mediated catalysis lead to the synthesis of sheet-structure-like polymers of the gross composition $R_2Si_2O_3$. The degree of cross-linking and the extension of these polymers can be varied by the controlled admixture of silandioles and silanoles. Thus, enzymatically tailored silicone structures can be produced having characteristic and regulateble properties.

The siloxane-scaffold can be linked to different kinds of hydrocarbon-residues. By this, its properties can be modified.

Due to their heat-resistibility and hydrophobicity, the silicones synthesised by the silicatein-mediated catalysis (not harmful according to experience) can be also used in cosmetic skincare and plastic surgery.

General literature: Brinker et al., Polydimethylsiloxane in der Lebens-und Genußmit-telindustrie, München: Dow Corning 1981.

5.7. Modification of the Properties of Cells by Transfection with a Silicatein-Gene/cDNA-Containing Plasimid By transfection of cells with a silicatein-gene/cDNA-containing plasmid, the properties of the cells can be changed, resulting in a use in the production of bone replacement materials (additionally by the co-polymerisation of silicatein-synthesised $SiO_2$ and polyphosphates, produced by transfection with a polyphosphate-kinase-cDNA containing plasmid).

5.8. Use of Recombinant Silicatein for the Synthesis of Nano-Structures from Amorphous Silicon Dioxide By means of the recombinant silicateins, the recombinant silicatein-fusion proteins or the purified silicatein, it is possible to synthesise specific two- and three-dimensional, sieve-, net-, cage- or otherwise formed structures from amorphous silicon dioxide, siloxanes or other silicon (IV)-[or gallium (IV)-, tin (IV)- or lead (IV)-]-compounds in a nanoscale wherein macromolecules (synthetic polymers or biopolymers) that are associated with these enzymes are used as "guiding tracks" for the synthesis. Such syntheses are also possible by using sponges or other silicatein-producing organisms kept in mariculture or in tanks, as well as organisms modified with genetic technology that initially are not able to synthesise silicate. The structures being formed can be used in nano-technology (for example as a "miniature sieve" for separation processes in nano-scale).

LEGENDS TO THE FIGURES

In the following, the explanatory legends for the accompanying drawings are given. The figures show:

FIG. 1:
cDNA together with deduced amino acid sequence for the suberites domuncula-silicatein.

FIG. 2:
Amino acid sequence of silicatein from the sponge suberites domuncula. Some sites at the protein are indicated [—] that, after truncation of the cDNA, lead to a strong increase of the expression of the recombinant protein. In addition, the amino acids of the catalytic triad (CT) as well as the cysteine-units are marked (•) that potentially lead to disulfide bridges.

FIG. 3:
Production of a recombinant silicatein-protein in E. coli. According to the method as indicated, the pure silicatein was obtained from crude extracts. Lane a: protein extract from non-induced cells [−IPTG]; lane b and lane c: protein extract from induced cells [+IPTG], 2.5 hours (lane b) and 8 hours (lane c) after addition of IPTG. Lane d: soluble protein extract of bacterial lysates after expression for 8 hours. Lane e: protein extract of the inclusion bodies. Lane f: purified silicatein derived from the inclusion bodies after purification of the protein on a Ni-NTA matrix. The molecular weight of the recombinant silicatein is approximately 33 kDa. On the left side, the molecular weight markers are indicated.

Figure 4:
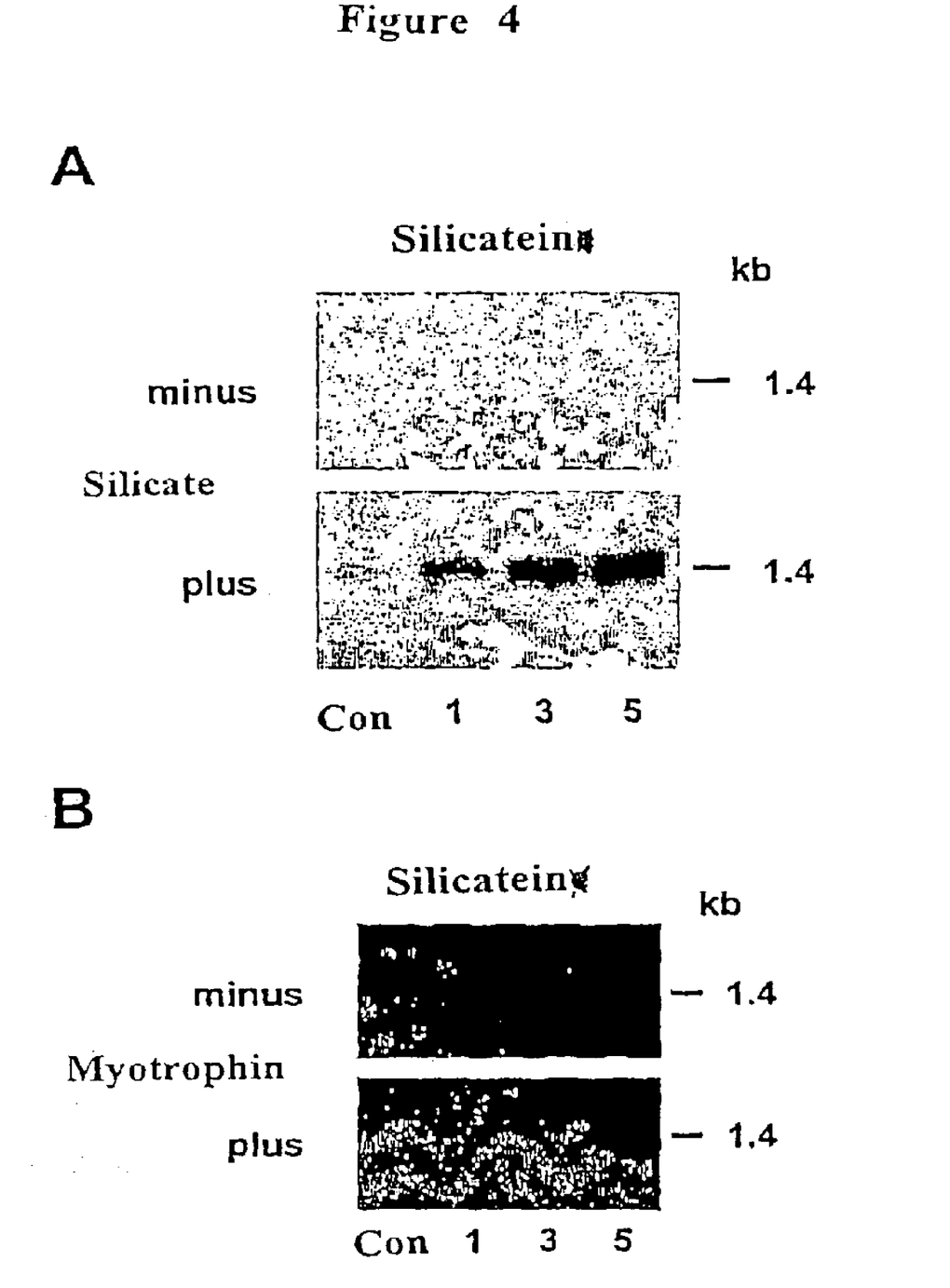
FIG. 4 illustrates the effect of recombinant myotrophin on the expression of silicatein and primmorphs.

FIG. 4:
(A) Concentration of transcripts for silicatein in primmorphs of S. domuncula. Primmorphs, which have formed from single cells after 5 day-incubation were incubated for 0 (controls; Con) to 5 days, either in the absence of exogeneous silicate (minus silicate) or in the presence of 60 μM Na-silicate (plus silicate). Then, the RNA was extracted and 5 μg of the total RNA were separated according to its size; after the blot-transfer, the hybridisation with the silicatein-probe of S. domuncula (SUBDOSILICA) was performed. (B) Effect of recombinant myotrophin on the expression of silicatein and primmorphs. The primmorphs were incubated for 0 (controls) up to 5 days in the absence (minus myotrophin) or presence of 1 μg/ml mytrophin (plus myotrophin). Then, Nothern-Blotting using the SUBDOSILICA-probe for determining the extent of expression of silicatein was performed.

Figure 5:
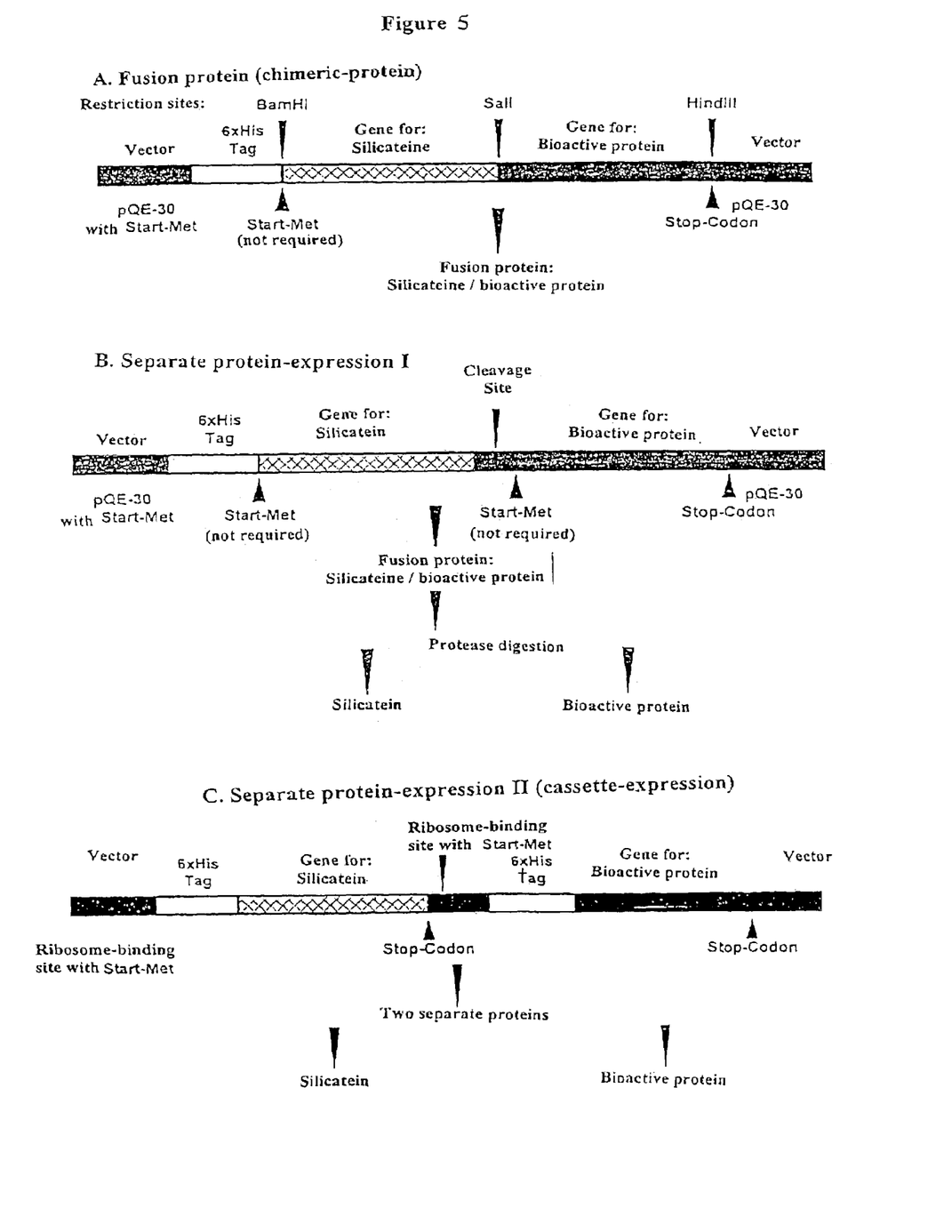
FIG. 5 shows the co-expression of silicatein and a gene that codes for a bioactive substance.

FIG. 5:
Co-expression of silicatein and the gene that codes for a bioactive substance (scheme). A. Production of the fusion protein silicatein-bioactive protein. Both cDNAs [silicatein and bioactive protein] were ligiated via a restriction site (e.g. SalI) and subsequently cloned into the restriction sites BamHI and HindIII of the vector pQE-30. The histidine-tag is located at the 5'-terminus. B. Separate protein expression. Both cDNAs were cloned into a suitable vector via a protease-restriction site. After expression and purification, the fusion protein is obtained separately by protease-digestion. C. Separate protein expression (as cassette-expression). Both cDNAs are separately expressed from the same construct and purified using the His-tags.

What is claimed is:

1. A method for producing a recombinant silicatein in a host cell, comprising:
   a) truncating a sequence from a terminal coding region of a cDNA sequence coding for silicatein to prepare a truncated cDNA sequence, and
   b) expressing the truncated cDNA sequence in the host cell so as to produce the recombinant silicatein in the host cell,
   wherein the truncation of the recombinant silicatein is positioned in front of the first potential disulfide-bridge and/or beyond the last potential disulfide-bridge, and wherein the silicatein is a truncated form of SEQ ID NO.:2.

2. The method as recited in claim 1, further comprising lysing the host cell.

3. The method as recited in claim 2, further comprising adding a protease-inhibitor during the lysing.

4. The method of claim 2, further comprising adding a protease-inhibitor after the lysing.

5. The method as recited in claim 1, further comprising isolating a functional recombinant silicatein.

6. The method as recited in claim 1, wherein the terminal coding region of the cDNA is an N-terminal coding region of the cDNA that extends up to the first disulfide bridge.

7. The method as recited in claim 1, wherein the terminal coding region of the cDNA is a C-terminal coding region of its cDNA that extends up to the last disulfide bridge.

8. The method as recited in claim 1, further comprising refolding the recombinant silicatein in the absence of lysozyme.

9. The method as recited in claim 1, further comprising inducing the expressing by adding silicate.

10. The method for the production of recombinant silicatein in a host cell as recited in claim 1, wherein the host cell is selected from the group consisting of *Escherichia coli*, yeast, mammals and primmorphs.

11. The method as recited in claim 10, wherein the primmorphs are selected from the group consisting of sponges and diatoms.

12. The method as recited in claim 1, wherein the host cell is a cell of *Cylindrotheca fusiformis*.

13. The method as recited in claim 1, wherein the host cell is a sponge.

14. The method as recited in claim 1, further comprising purifying the silicatein using a polyclonal antibody.

15. The method as recited in claim 14, wherein the polyclonal antibody is coupled to a solid phase.

16. The method as recited in claim 1, further comprising purifying the silicatein using a histidine-tag.

17. The method as recited in claim 1, further comprising purifying the silicatein by affinity chromatography using a histidine-tag.

18. The method for the production of recombinant silicatein in a host cell as recited in claim 1, wherein the recombinant silicatein is expressed as a fusion protein.

19. The method for the production of recombinant silicatein in a host cell as recited in claim 18, wherein the recombinant silicatein comprises a protease cleavage-site.

20. A recombinant silicatein, produced using the method recited in claim 1.

21. A method for production of at least one of amorphous silicon dioxide, siloxanes, silicon (IV)-compounds, silapharmaca, gallium, (IV)-compounds, tin (IV)-compounds, lead (IV)-compounds and mixed polymers thereof, comprising converting with a silicatein produced using the method recited in claim 1 a silicatein substrate selected from the group consisting of tetraalkoxysilanes, trialkoxysilanoles, dialkoxysilandioles, monoalkoxysilantrioles, alkyl-trialkoxysilanes, aryl-trialkoxysilanes, alkyl-dialkoxysilanoles, aryl-dialkoxysilanoles, alkyl-monoalkoxysilandioles, aryl-monoalkoxysilandioles, alkyl-substituted alkoxy compounds of gallium (IV), aryl-substituted alkoxy compounds of gallium (IV), alkyl-substituted alkoxy compounds of tin (IV), aryl-substituted alkoxy compounds of tin (IV), alkyl-substituted alkoxy compounds of lead (IV), aryl-substituted alkoxy compounds of lead (IV) and combinations thereof.

22. The method as recited in claim 21, wherein the silicon dioxide is selected from the group consisting of a silicic acid, a silicate and combinations thereof.

23. The method as recited in claim 21, wherein the silicatein substrate comprises a defined mixture.

24. The method as recited in claim 21, wherein the silicatein is immobilized on a surface comprised of a material selected from the group consisting of glass, metals, metal oxides, plastics, biopolymers and combinations thereof.

25. The method as recited in claim 21, further comprising purifying the at least one of amorphous silicon dioxide, siloxanes, silicon (IV)-compounds, gallium (IV)-compounds, tin (IV)-compounds, lead (IV)-compounds and mixed polymers thereof.

26. The method as recited in claim 1, wherein the silicatein is a truncated form of SEQ ID NO.: 2 having an N-terminal truncation at a position up to amino acid 135 and/or a C-terminal truncation at a position beyond amino acid 319.

\* \* \* \* \*

UNITED STATES PATENT AND TRADEMARK OFFICE
CERTIFICATE OF CORRECTION

PATENT NO.          : 7,169,589 B2
APPLICATION NO.  : 10/343104
DATED                    : January 30, 2007
INVENTOR(S)         : Werner E. G. Müller et al.

It is certified that error appears in the above-identified patent and that said Letters Patent is hereby corrected as shown below:

Column 4,
Line 57, "sythesis product" should read --synthesis product--.

Column 6,
Line 7, "recombnant proteins" should read --recombinant proteins--.

Column 11,
Line 37, "regulateble" should read --regulateable--.
Line 49, "Plasimid" should read --Plasmid--.

Signed and Sealed this

Twenty-eighth Day of August, 2007

JON W. DUDAS
*Director of the United States Patent and Trademark Office*